United States Patent
Nishiwaki et al.

(10) Patent No.: US 7,298,550 B2
(45) Date of Patent: Nov. 20, 2007

(54) DICHROIC MIRROR, FLUORESCENCE FILTER SET, AND FLUOROSCOPY APPARATUS

(75) Inventors: Daisuke Nishiwaki, Hino (JP); Kei Kikuchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 37 days.

(21) Appl. No.: 11/184,814

(22) Filed: Jul. 20, 2005

(65) Prior Publication Data

US 2006/0028729 A1    Feb. 9, 2006

(30) Foreign Application Priority Data

Jul. 22, 2004    (JP)    .............. 2004-214620

(51) Int. Cl.
*G02B 21/00*    (2006.01)

(52) U.S. Cl. .................. 359/384; 359/634; 359/580; 359/588; 359/589; 359/584; 359/585; 359/586; 359/587

(58) Field of Classification Search ........ 359/384–589, 359/359, 634
See application file for complete search history.

(56) References Cited

U.S. PATENT DOCUMENTS

| | | | | |
|---|---|---|---|---|
| 3,853,386 | A * | 12/1974 | Ritter et al. ................ | 359/588 |
| 3,973,827 | A * | 8/1976 | Uetake ........................ | 359/355 |
| 5,339,198 | A * | 8/1994 | Wheatly et al. ............ | 359/359 |
| 5,341,238 | A * | 8/1994 | Trost et al. ................. | 359/359 |
| 5,371,624 | A * | 12/1994 | Nagano et al. ............. | 359/389 |
| 5,710,663 | A * | 1/1998 | Kawasaki ................... | 359/389 |
| 6,262,837 | B1 * | 7/2001 | Nagano et al. ............. | 359/368 |

FOREIGN PATENT DOCUMENTS

| | | |
|---|---|---|
| JP | 54-110855 | 8/1979 |
| JP | 61-045202 | 3/1986 |
| JP | 62-027361 | 6/1987 |
| JP | 11-202127 | 7/1999 |

\* cited by examiner

*Primary Examiner*—Scott J. Sugarman
*Assistant Examiner*—James R Greece
(74) *Attorney, Agent, or Firm*—Kenyon & Kenyon LLP (57) ABSTRACT

The invention provides a dichroic mirror having a transmission characteristic in which a step due to splitting of P-polarized and S-polarized light can be reduced and having a fluorescence-transmitting band extending to long wavelengths. The invention also provides a fluorescence filter set that can be constructed of environmentally conscious glass materials that do no use harmful substances, such as lead, and a fluoroscopy apparatus including such a fluorescence filter set. The dichroic mirror comprises a transparent substrate and a dielectric multilayer film formed by alternately laminating high-refractive-index layers and low-refractive-index layers on the transparent substrate. The dielectric multilayer film includes from 50 to 150 alternately laminated high-refractive-index layers and low-refractive-index layers each having an optical film thickness from $1.5\lambda_0/4$ to $2.5\lambda_0/4$, where $\lambda_0$ is a design wavelength, and the dichroic mirror has a reflection band located at wavelengths shorter than the design wavelength.

10 Claims, 8 Drawing Sheets

DICHROIC MIRROR, FLUORESCENCE FILTER SET, AND FLUOROSCOPY APPARATUS

BACKGROUND OF THE INVENTION

1. Field of the Invention

The present invention relates to a dichroic mirror, to a fluorescence filter set, and to a fluoroscopy apparatus, such as a microscope or endoscope for fluoroscopy, a measurement device for measuring fluorescence intensity, and so forth.

This application is based on Japanese Patent Application No. 2004-214620, the content of which is incorporated herein by reference.

2. Description of Related Art

Known dichroic mirrors according to the related art include those disclosed below, for example.

A dichroic mirror described in Japanese Unexamined Patent Application Publication No. HEI-11-202127 includes a multilayer film formed, on a transparent substrate, by alternately laminating high-refractive-index layers, intermediate-refractive-index layers, and low-refractive-index layers having optical film thicknesses equal to ¼ of a design center wavelength $\lambda_0$.

A dichroic mirror described in Japanese Unexamined Patent Application Publication No. SHO-61-45202 includes alternating layers formed, on a substrate, by alternately laminating high-refractive-index layers having an optical film thickness equal to ¼ of a reference wavelength $\lambda_0$, and low-refractive-index layers having an optical film thickness equal to ¾ of the reference wavelength $\lambda_0$.

A dichroic mirror described in Japanese Unexamined Patent Application Publication No. SHO-54-110855 (Japanese Examined Patent Application Publication No. SHO-62-27361) includes alternating layers formed by alternately laminating, on a substrate, high-refractive-index layers having optical film thicknesses equal to ¼ and ¾ of a reference wavelength $\lambda_0$, and low-refractive-index layers having optical film thicknesses equal to ¼ and ¾ of the reference wavelength $\lambda_0$.

BRIEF SUMMARY OF THE INVENTION

One effective method in fluoroscopy is to set a reflection band for the excitation light and a transmission band for the fluorescence of the dichroic mirror as close to each other as possible, because the wavelength of excitation light irradiating a specimen and the wavelength of fluorescence produced by a fluorescent substance in the specimen are close to each other.

However, the dichroic mirror described in Japanese Unexamined Patent Application Publication No. HEI-11-202127 suffers from the drawback that, if the dichroic mirror is placed at an angle of about 45° with respect to the incident optical axis of the excitation light, a relatively large step occurs in the transmission characteristic due to splitting of P-polarized and S-polarized light.

If a relative large step occurs in the transmission characteristic due to splitting of P-polarized and S-polarized light, the reflection band for excitation light an d the transmission band for fluorescence are separated by a distance corresponding to the width of the region where the step is formed. As a result, there is a problem in that, if the transmission characteristic is set at the short-wavelength side in order to efficiently collect weak fluorescence emitted from the specimen, part of the excitation light will be transmitted by the dichroic mirror, whereas if the transmission characteristic is set at the long-wavelength side in order to completely reflect the excitation light, part of the fluorescence will be reflected by the dichroic mirror.

When part of the excitation light is transmitted by the dichroic mirror, excitation light scattered by components and so on enters the observation optical system from various directions. Therefore, it is necessary to prevent the excitation light from entering the observation optical system by using an absorption filter formed of colored glass having a spectral characteristic with low angular dependence. However, colored glass cannot be formed without using harmful substances, such as lead and cadmium, which is contrary to the recent trend of ensuring environmental protection, for example, forming microscopes only of environmentally conscious materials that are friendly to the environment. Also, since three types of film are used, namely, a high-refractive-index film, an intermediate-refractive-index film, and a low-refractive-index film, there is another drawback in that the fabrication becomes complicated.

Moreover, when alternately laminating high-refractive-index layers and low-refractive-index layers with thicknesses equal to ¼ and ¾ of the reference wavelength $\lambda_0$, as in the dichroic mirrors described in Japanese Unexamined Patent Application Publication No. SHO-61-45202 and Japanese Examined Patent Application Publication No. SHO-62-27361, it is possible to reduce the step in the transmission characteristic due to splitting of P-polarized and S-polarized light, like the dichroic mirror described in Japanese Unexamined Patent Application Publication No. HEI-11-202 127; however, the rise in the transmission characteristic is gentle.

The present invention has been conceived in light of the circumstances described above, and an object thereof is to provide a dichroic mirror having a transmission characteristic in which a step due to splitting of P-polarized and S-polarized light can be reduced and having a fluorescence-transmitting band extending to long wavelengths. Another object is to provide a fluorescence filter set that can be constructed of environmentally conscious glass materials that do no use hazardous substances, such as lead, and a fluoroscopy apparatus including such a fluorescence filter set, such as a microscope or endoscope, or a measurement device for measuring fluorescence intensity.

In order to achieve the objects described above, the present invention provides the following solutions.

The present invention provides a dichroic mirror including a transparent substrate; and a dielectric multilayer film formed by alternately laminating high-refractive-index layers and low-refractive-index layers on the transparent substrate. The dielectric multilayer film includes from 50 to 150 alternately laminated high-refractive-index layers and low-refractive-index layers each having an optical film thickness from $1.5\lambda_0/4$ to $2.5\lambda_0/4$, where $\lambda_0$ is a design wavelength, and wherein the dichroic mirror has a reflection band located at wavelengths shorter than the design wavelength.

With the dichroic mirror according to the present invention, the width of a higher-harmonic reflection band at or above the second harmonic can be increased and used as the reflection band. In the higher-harmonic reflection band, even if the dichroic mirror is tilted with respect to the incident optical axis of the excitation light, a step in the transmission characteristic due to splitting of P-polarized and S-polarized light components can be reduced, which in turn allows the reflection band for the excitation light and the transmission band for the fluorescence to be made close to each other. As a result, substantially all of the excitation light can be reflected and the fluorescence can be efficiently transmitted. In addition, a fluorescence-transmitting band extending to longer wavelengths can be ensured, to allow a wider range of use, even for collecting long-wavelength fluorescence.

The present invention also provides a fluorescence filter set including a first wavelength-selecting member for selectively transmitting excitation light of a first wavelength; a dichroic mirror described above, for reflecting the excitation light transmitted by the first wavelength-selecting member in a direction orthogonal to an incident direction and for transmitting fluorescence returning from the reflection direction; and a second wavelength-selecting member for selectively transmitting the fluorescence transmitted by the dichroic mirror.

With the fluorescence filter set according to this aspect of the present invention, when the excitation light selectively transmitted by the first wavelength-selecting member is incident on the dichroic mirror, it is reflected in a direction orthogonal to the incident direction and is irradiated in the reflection direction. When the fluorescence returning from the reflection direction is incident on the dichroic mirror, it is transmitted thereby and is incident on the second wavelength-selecting member placed at the subsequent position, which selectively transmits only the fluorescence.

In this case, according to the present invention, even if the angle of incidence of the excitation light to the dichroic mirror is relatively large, because the step in the transmission characteristic due to splitting of P-polarized and S-polarized light is reduced, it is possible to reflect substantially all of the excitation light. As a result, almost no excitation light is incident on the second wavelength-selecting member from various directions, and therefore, it is not necessary to use colored glass having a spectral characteristic with no angular dependence. Accordingly, the fluorescence filter set can be constructed using only environmentally conscious glass materials that do not include harmful substances, such as lead or cadmium.

According to another aspect, the present invention provides a fluoroscopy apparatus, such as a microscope or endoscope or a measurement device for measuring fluorescence intensity, including: a light source; a fluorescence filter set described above, for reflecting excitation light from the light source and for transmitting fluorescence returning from the reflection direction; an objective optical system for irradiating a specimen with the excitation light reflected by the fluorescence filter set; and an observation optical system for observing the fluorescence returning from the specimen and transmitted by the objective optical system and the fluorescence filter set.

With the fluoroscopy apparatus according to the present invention, when light emitted from the light source is incident on the fluorescence filter set, the excitation light selectively transmitted by the first wavelength-selecting member is reflected by the dichroic mirror and is irradiated onto the specimen via the objective optical system. In the specimen, a fluorescent substance injected in advance or an autofluorescence substance in the specimen is excited by the excitation light and fluorescence is produced. The fluorescence produced in the specimen returns via the objective optical system, enters the fluorescence filter set, is transmitted by the dichroic mirror, passes through the second wavelength-selecting member, and is introduced to the observation optical system.

With the fluoroscopy apparatus according to the present invention, since substantially all of the excitation light from the light source is reflected by the dichroic mirror, no excitation light is incident on the second wavelength-selecting member from various directions, and therefore, it is possible to eliminate substantially all of the excitation light incident on the observation optical system, without using colored glass in the second wavelength-selecting member. As a result, the glass members of the fluoroscopy apparatus can be constructed using only environmentally conscious glass materials that do not include harmful substances, and it is therefore possible to construct a fluoroscopy apparatus that is suitable from the viewpoint of environmental protection. Also, it is possible to almost completely prevent the excitation light from entering the observation optical system, even without using colored glass elements, thus allowing clear, flare-free observation images to be obtained.

With the dichroic mirror according to the present invention described above, the step in the transmission characteristic due to splitting of P-polarized and S-polarized light can be reduced, and a fluorescence-transmitting band extending to long wavelengths can be ensured. Also, with the fluorescence filter set and the fluoroscopy apparatus according to the aspects of the invention described above, the excitation light is not transmitted to the observation optical system, which affords an advantage in that it is possible to obtain clear observation images having little noise, such as flare. In addition, an advantage is afforded in that the glass members can be constructed using environmentally conscious materials that do not include harmful substances, such as lead, which is preferable from the viewpoint of environmental protection.

DETAILED DESCRIPTION OF THE INVENTION

A dichroic mirror, a fluorescence filter set, and a fluoroscopy apparatus according to an embodiment of the present invention will be described below with reference to FIGS. 1 to 8.

Figure 1:
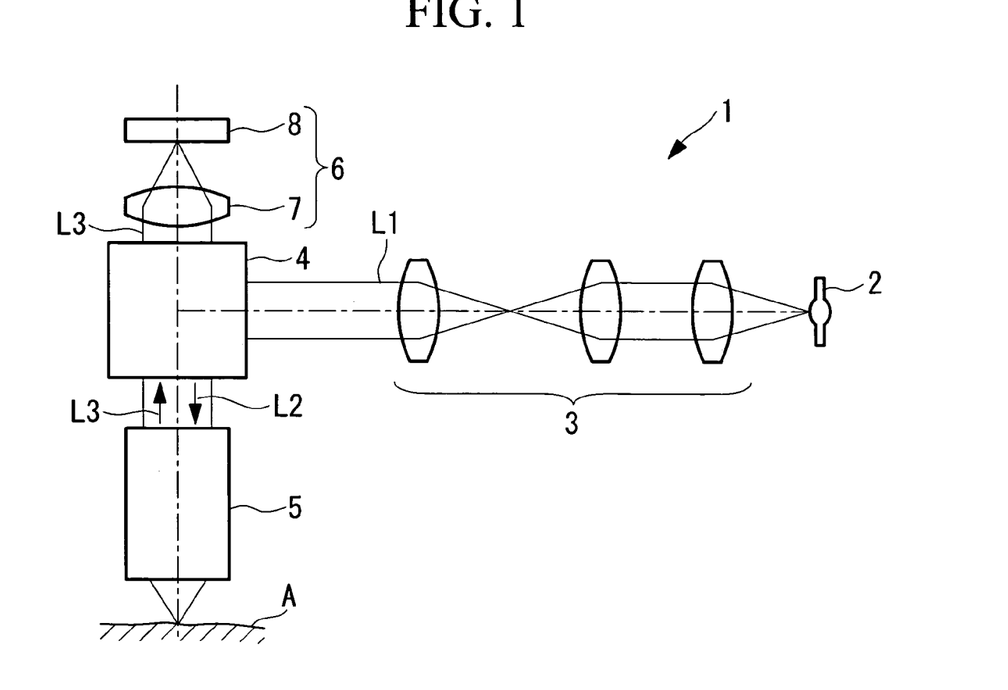
FIG. 1 shows the configuration of a fluorescence microscope according to an embodiment of the present invention.

The overall configuration of a fluoroscopy apparatus 1 according to this embodiment is shown in FIG. 1.

As shown in FIG. 1, the fluoroscopy apparatus 1 according to this embodiment includes a light source 2; an illumination optical system 3 for efficiently guiding light L1 emitted from the light source 2; a fluorescence filter set 4 to which the light L1 from the illumination optical system is introduced and which emits excitation light L2 in a direction perpendicular to the incident direction of the light L1, and in addition, which transmits in a straight line fluorescence L3 returning from the direction in which the excitation light L2 is emitted; an objective optical system 5 for focusing the emitted excitation light L2 onto a specimen A; and an observation optical system 6 for observing the fluorescence L3 produced in the specimen A and transmitted through the objective optical system 5 and the fluorescence filter set 4. The observation optical system 6 includes an imaging lens 7 and a detecting device 8, for example, a CCD camera.

Figure 2:
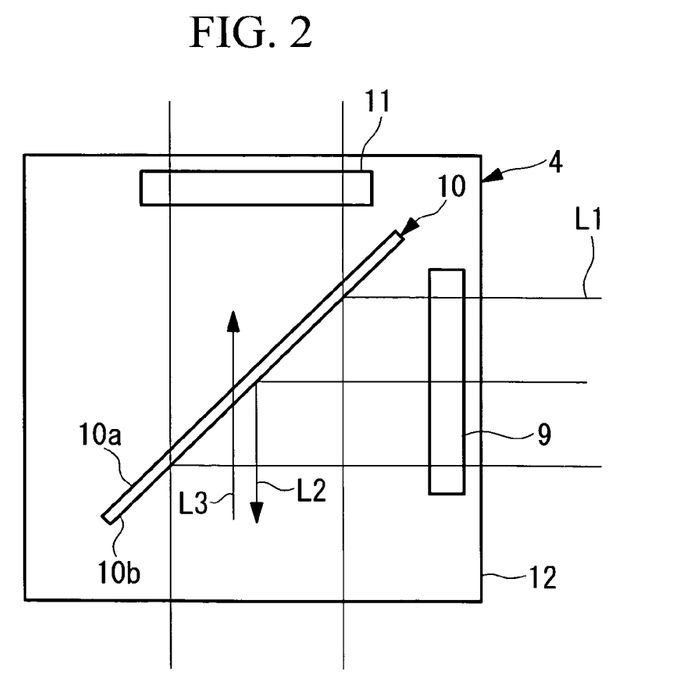
FIG. 2 shows the configuration of a fluorescence filter set according to an embodiment of the present invention, which is used in the fluorescence microscope in FIG. 1.

As shown in FIG. 2, the fluorescence filter set 4 according to this embodiment has a configuration in which a first optical filter (first wavelength-selecting member) 9; a dichroic mirror 10; and a second optical filter (second wavelength-selecting member) 11 are disposed inside a casing 12. The first optical filter 9 transmits only excitation light L2 of a specific wavelength from the light L1 incident thereon from the light source 2. The dichroic mirror 10 is disposed at an angle of 45° with respect to the incident direction so as to reflect the excitation light L2 transmitted by the first optical filter 9 in a direction orthogonal to the incident direction thereof. The second optical filter 11 selectively transmits the fluorescence L3 transmitted by the dichroic mirror 10.

The dichroic mirror 10 includes a dielectric multilayer film 10b, formed by alternately laminating high-refractive-index layers and low-refractive-index layers on a planar transparent substrate 10a.

The high-refractive-index layers are dielectric layers formed of a high-refractive-index material with a refractive index of 2.0 or more. The low-refractive-index layers are dielectric layers formed of a low-refractive-index material with a refractive index of 1.5 or less. The optical film thicknesses of these high-refractive-index and low-refractive-index layers are set to be from $1.5\lambda_0/4$ to $2.5\lambda_0/4$, with respect to a design wavelength $\lambda_0$. The dielectric multilayer film 10b preferably includes alternating layers formed by alternately laminating 50 to 150 high-refractive-index layers and low-refractive-index layers.

Here, the design wavelength $\lambda_0$ is a first-harmonic central wavelength at an incident angle of 0°.

The dichroic mirror 10 has a reflection band at the short wavelength side of the design wavelength $\lambda_0$. In other words, it does not use the first-harmonic wavelength band located close to the design wavelength $\lambda_0$ as a reflection band B; rather, it uses a wavelength band of a second harmonic or higher, which appears at the short wavelength side of the design wavelength $\lambda_0$, as the reflection band B.

The operation of the dichroic mirror 10, the fluorescence filter set 4, and the fluoroscopy apparatus 1 according to this embodiment, having the above-described configuration, will be described below.

A dichroic mirror of the related art uses a wavelength band where the transmission characteristic is approximately 0%, which appears in the first-harmonic wavelength band located close to the design wavelength $\lambda_0$, as the reflection band B. The reason for this is that a region where the transmission characteristic is approximately 0% in a wavelength band of a second high harmonic or higher, which appears at the short wavelength side of the design wavelength $\lambda_0$, is extremely narrow, and therefore, use of such a wavelength band as the reflection band B is completely out of the question.

Conversely, because the dichroic mirror 10 according to this embodiment is formed by alternating 50 to 150 high-refractive-index layers and low-refractive-index layers, it is possible to ensure a sufficiently wide wavelength band where the transmission characteristic is approximately 0% in a wavelength band of this second harmonic or higher, and this band can thus be used as the reflection band B.

Figure 3:
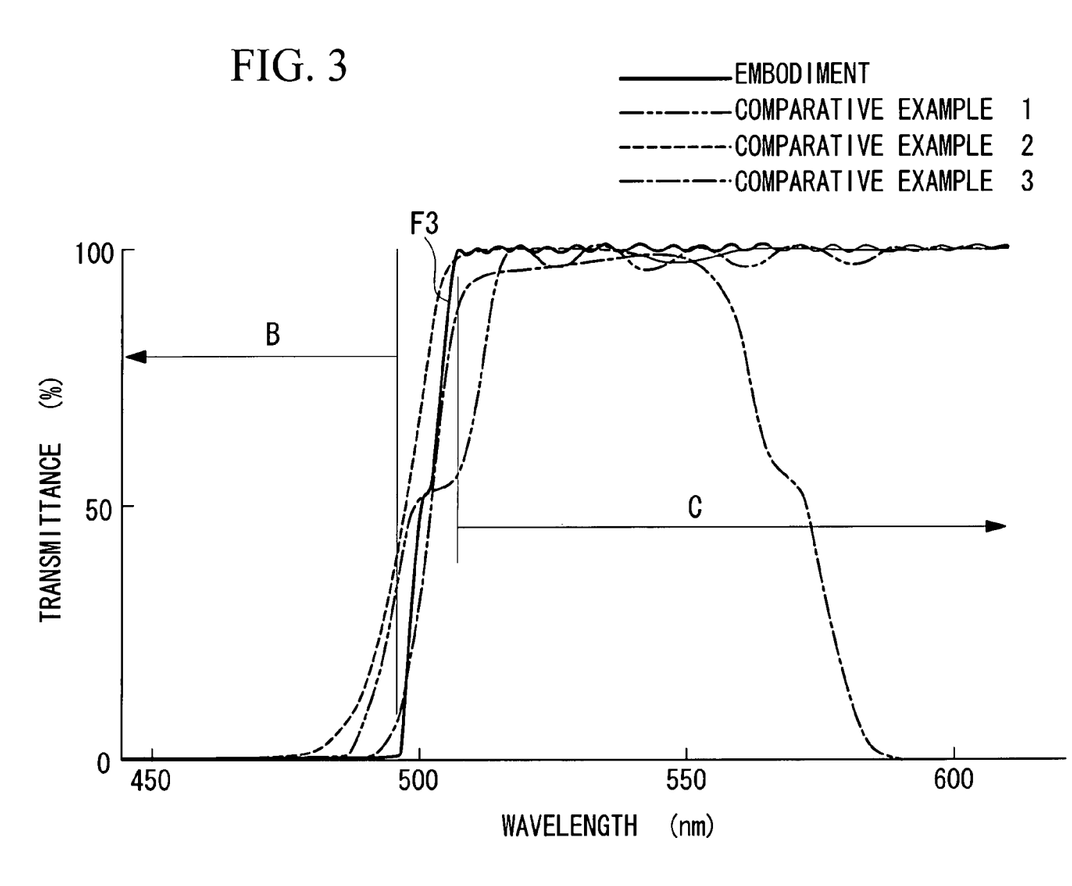
FIG. 3 schematically shows a transmission characteristic of a dichroic mirror according to an embodiment of the present invention, which is used in the fluorescence filter set in FIG. 2, compared to the transmission characteristics of dichroic mirrors of the related art.

As a result, the dichroic mirror 10 has an ideal transmission characteristic, as schematically shown by the characteristic in FIG. 3. Comparative Example 1 in FIG. 3 is an example in which the optical film thicknesses of the high-refractive-index layer and the low-refractive-index layer are both $\lambda_0/4$, and Comparative Examples 2 and 3 are examples in which the optical film thicknesses of the high-refractive-index layer and the low-refractive-index layer are $\lambda_0/4$ and $3\lambda_0/4$, respectively. The number of alternately laminated layers in each case is about 20.

In Comparative Example 1, a large step occurs in the transmission characteristic due to splitting of P-polarized and S-polarized light, as a result of disposing the dichroic mirror at an angle of 45° with respect to the incident optical axis of the excitation light L2. Comparative Examples 2 and 3 have no step but they suffer from the drawback that in the reflection band B, the transmission characteristics rise gently from approximately 0%, and the transmission characteristics in a fluorescence-transmitting band C gradually reach about 100%. In particular, there is a problem with Comparative Example 3 in that the transmittance in the fluorescence-transmitting band C drops suddenly at longer wavelengths without reaching 100%.

Conversely, in the dichroic mirror 10 according to this embodiment, from the reflection band B where the transmittance is approximately 0%, exhibits a small step due to splitting of P-polarized and S-polarized light, and quickly reaches about 100% in the fluorescence-transmitting band C. Moreover, the fluorescence-transmitting band C extends to long wavelengths.

Therefore, with the dichroic mirror according to this embodiment, it is possible to make the reflection band B and the fluorescence-transmitting band C close to each other. Since the wavelength band of the excitation light L2 and the wavelength band of the fluorescence L3 produced by that excitation light L2 are close to each other, making the reflection band B and the fluorescence-transmitting band C close to each other allows the excitation light L2 to be irradiated onto the specimen A in such a way that the fluorescence L3 is efficiently produced in the specimen A.

Figure 4:
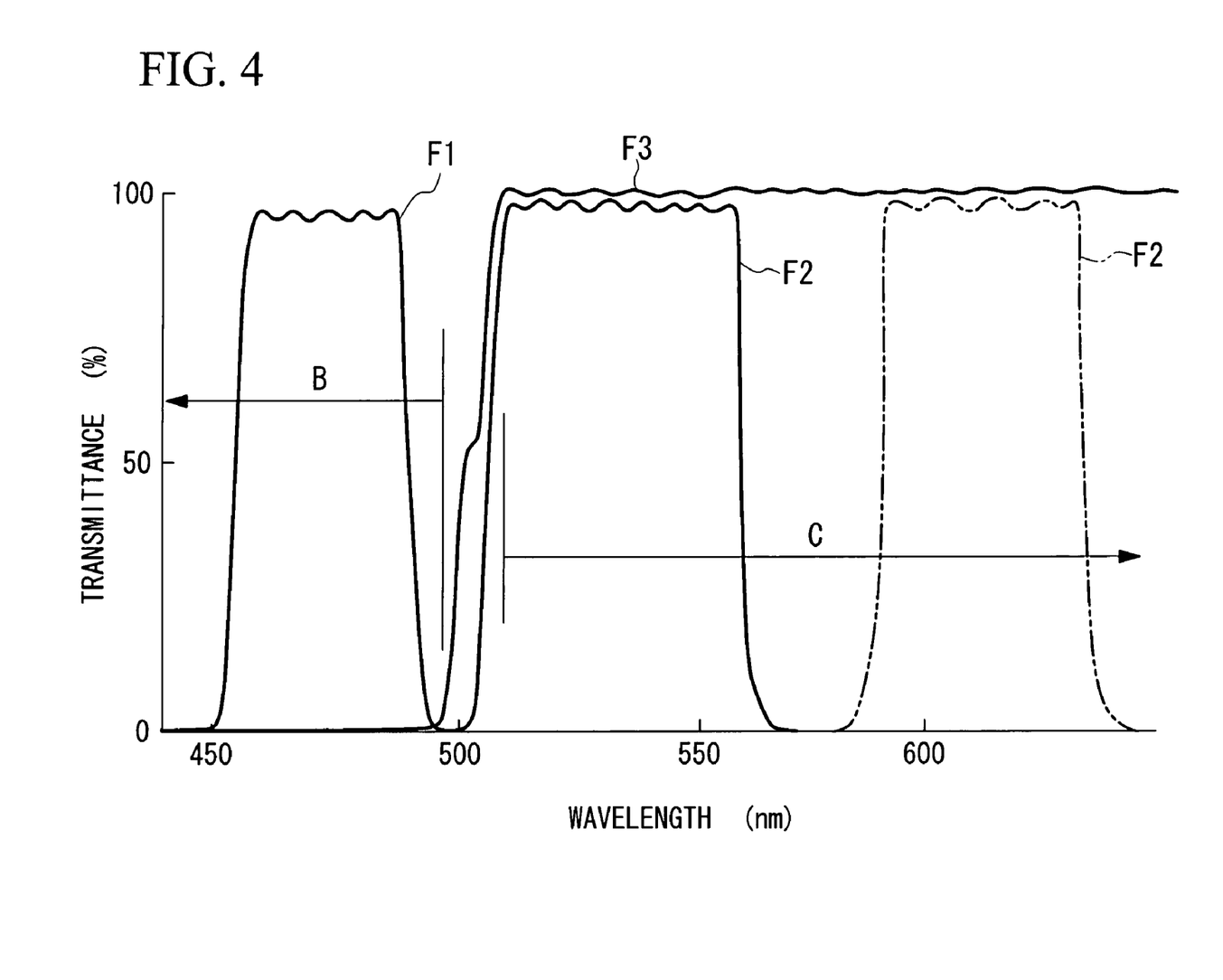
FIG. 4 schematically shows together transmission characteristics of first and second optical filters and a dichroic mirror constituting the fluorescence filter set in FIG. 2.

As shown in FIG. 4, with the fluorescence filter set 4 according to this embodiment, which uses the dichroic mirror 10, it is possible to set a transmission characteristic F1 for the excitation light L2 selected by the first optical filter 9 and a transmission characteristic F2 for the fluorescence L3 selected by the second optical filter 11 close to each other. In other words, because the transmission characteristic F3 of the dichroic mirror 10 rises sharply from the reflection band B where the transmittance is approximately 0%, even if the transmission characteristic F1 of the first optical filter 9 is set at comparatively longer wavelengths, the problem of the excitation light L2 transmitted by the first optical filter 9 being transmitted by the dichroic mirror 10 can be prevented.

Therefore, since the excitation light L2 is not transmitted by the dichroic mirror 10, it is not scattered inside the casing 12, and the excitation light L2 can thus be prevented from passing through the second optical filter 11 without using colored glass having low angular dependency as the second optical filter 11.

Also, because the transmission characteristic F3 of the dichroic mirror 10 quickly reaches the fluorescence-transmitting band C where the transmittance is approximately 100%, even though the transmission characteristic F2 of the second optical filter 11 is set at comparatively shorter wavelengths, part of the fluorescence L3 that can pass through the second optical filter 11 can be prevented from being reflected at the dichroic mirror 10, which allows the fluorescence L3 to be efficiently collected.

Furthermore, since the transmission characteristic F3 of the dichroic mirror 10 has the fluorescence-transmitting band C which extends to long wavelengths, it is possible to construct a fluorescence filter set 4 that is capable of multiple uses, even when to collect long-wavelength fluorescence L3.

Also, since it is possible to set the reflection band B and the fluorescence-transmitting band C of the dichroic mirror 10 close to each other, an advantage is afforded in that the intensity of the fluorescence L3 reaching the CCD camera 8 can be increased, which allows bright fluorescence images to be obtained.

Moreover, since colored glass is not used, the glass components constituting the fluoroscopy apparatus 1 can be fabricated using only environmentally conscious materials that do not include harmful substances, such as lead and cadmium, which provides an advantage in that it is possible to construct a fluoroscopy apparatus 1 that is desirable from the viewpoint of environmental protection.

EXAMPLES

First Example

Figure 5:
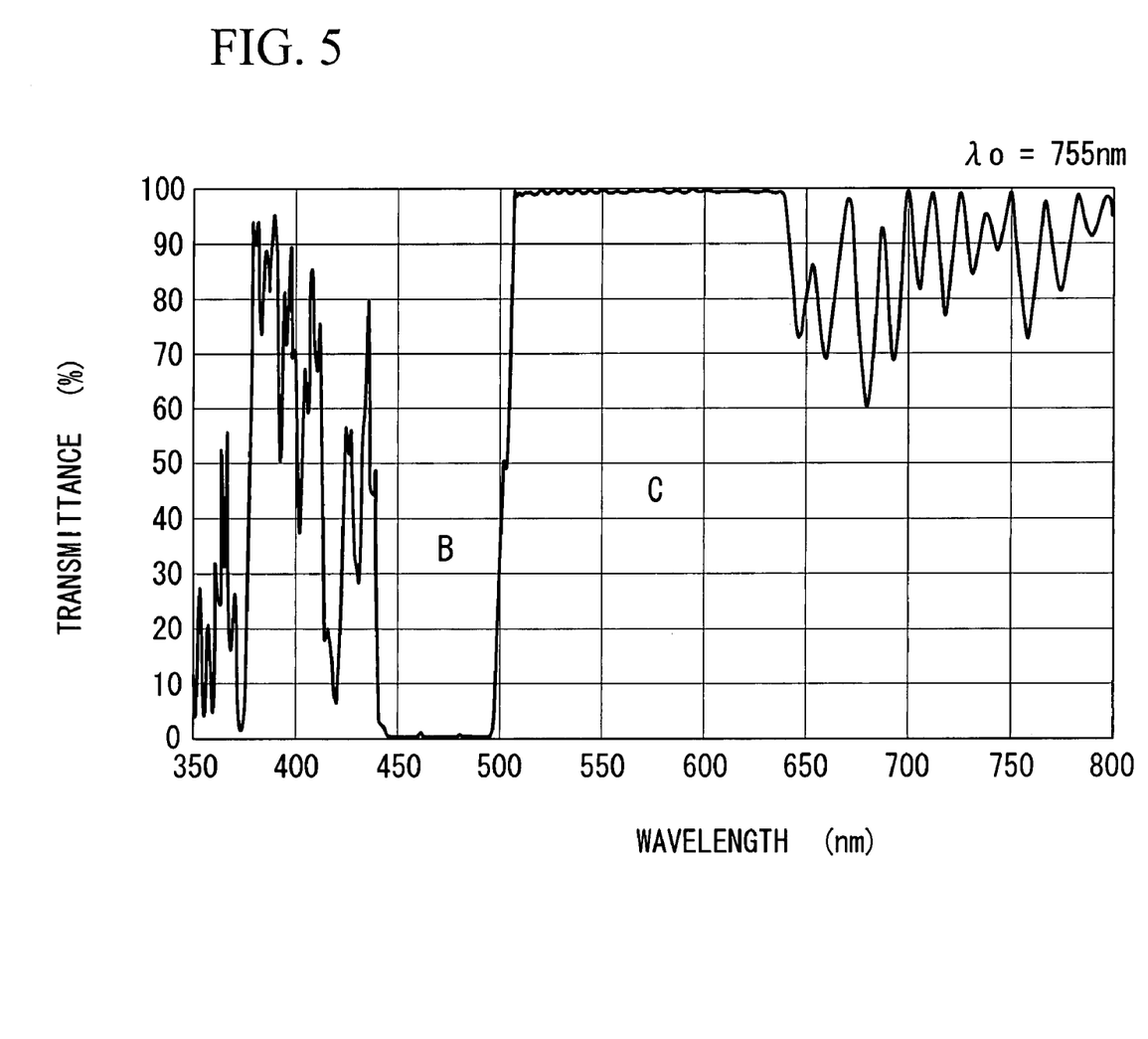
FIG. 5 shows a transmission characteristic of the dichroic mirror in FIG. 3, according to a first Example.

The optical film thicknesses of the dichroic multilayer film 10b according to a first Example, used in the dichroic mirror 10 according to the embodiment described above, are shown in Table 1. The transmission characteristic F3 of the dichroic mirror 10 according to the first Example is shown in FIG. 5.

TABLE 1

| LAYER NUMBER | TYPE | $\lambda_0 = 755$ nm OPTICAL FILM THICKNESS (×$\lambda_0$/4) |
|---|---|---|
| 1 | H | 1.70719 |
| 2 | L | 2.18534 |
| 3 | H | 1.85964 |
| 4 | L | 2.18116 |
| 5 | H | 1.91783 |
| 6 | L | 2.13518 |
| 7 | H | 1.92256 |
| 8 | L | 1.94514 |
| 9 | H | 1.63429 |
| 10 | L | 1.83579 |
| 11 | H | 1.92985 |
| 12 | L | 2.01307 |
| 13 | H | 2.03473 |
| 14 | L | 1.97494 |
| 15 | H | 1.91585 |
| 16 | L | 1.85511 |
| 17 | H | 1.84039 |
| 18 | L | 1.9242 |
| 19 | H | 2.04608 |
| 20 | L | 1.95675 |
| 21 | H | 2.0729 |
| 22 | L | 1.95715 |
| 23 | H | 1.89304 |
| 24 | L | 1.84951 |
| 25 | H | 1.8312 |
| 26 | L | 1.98136 |
| 27 | H | 1.99925 |

TABLE 1-continued

| LAYER NUMBER | TYPE | $\lambda_0 = 755$ nm OPTICAL FILM THICKNESS (×$\lambda_0$/4) |
|---|---|---|
| 28 | L | 2.07597 |
| 29 | H | 2.001 |
| 30 | L | 2.13986 |
| 31 | H | 1.97666 |
| 32 | L | 2.17144 |
| 33 | H | 1.97648 |
| 34 | L | 2.15612 |
| 35 | H | 1.99265 |
| 36 | L | 2.14963 |
| 37 | H | 1.99797 |
| 38 | L | 2.15201 |
| 39 | H | 1.98005 |
| 40 | L | 2.16657 |
| 41 | H | 1.98304 |
| 42 | L | 2.15482 |
| 43 | H | 1.98848 |
| 44 | L | 2.13802 |
| 45 | H | 2.00162 |
| 46 | L | 2.14837 |
| 47 | H | 1.97352 |
| 48 | L | 2.16167 |
| 49 | H | 1.96414 |
| 50 | L | 2.16402 |
| 51 | H | 1.98608 |
| 52 | L | 2.09391 |
| 53 | H | 2.03025 |
| 54 | L | 2.02201 |
| 55 | H | 2.07617 |
| 56 | L | 1.93539 |
| 57 | H | 2.08068 |
| 58 | L | 0.95707 |

Table 1 and FIG. 5, which assume a design wavelength $\lambda_0$=755 nm, show a case where a third-harmonic band is used as the reflection band for the excitation light, and the values shown in Table 1 represent coefficients of the optical film thickness of each layer expressed in $\lambda_0$/4 units. Layers for which these coefficients range from 1.5 to 2.5 form alternating layers, and the layer having a coefficient other than these is an adjustment layer. The coefficients are shown in order from the transparent substrate 10a side. By setting the coefficient for the final layer in contact with air to be about half or less of the coefficients for the other layers, it is possible to achieve a transmission characteristic F3 that is highly stable at longer wavelengths.

The symbol H in Table 1 indicates a high-refractive-index layer, and the symbol L indicates a low-refractive index layer.

The film forming method used to fabricate the dichroic mirror may be ion-assisted deposition, RF ion plating, RF sputtering, ion-beam sputtering, and so on, so long as the same results are achieved.

Second Example

Figure 6:
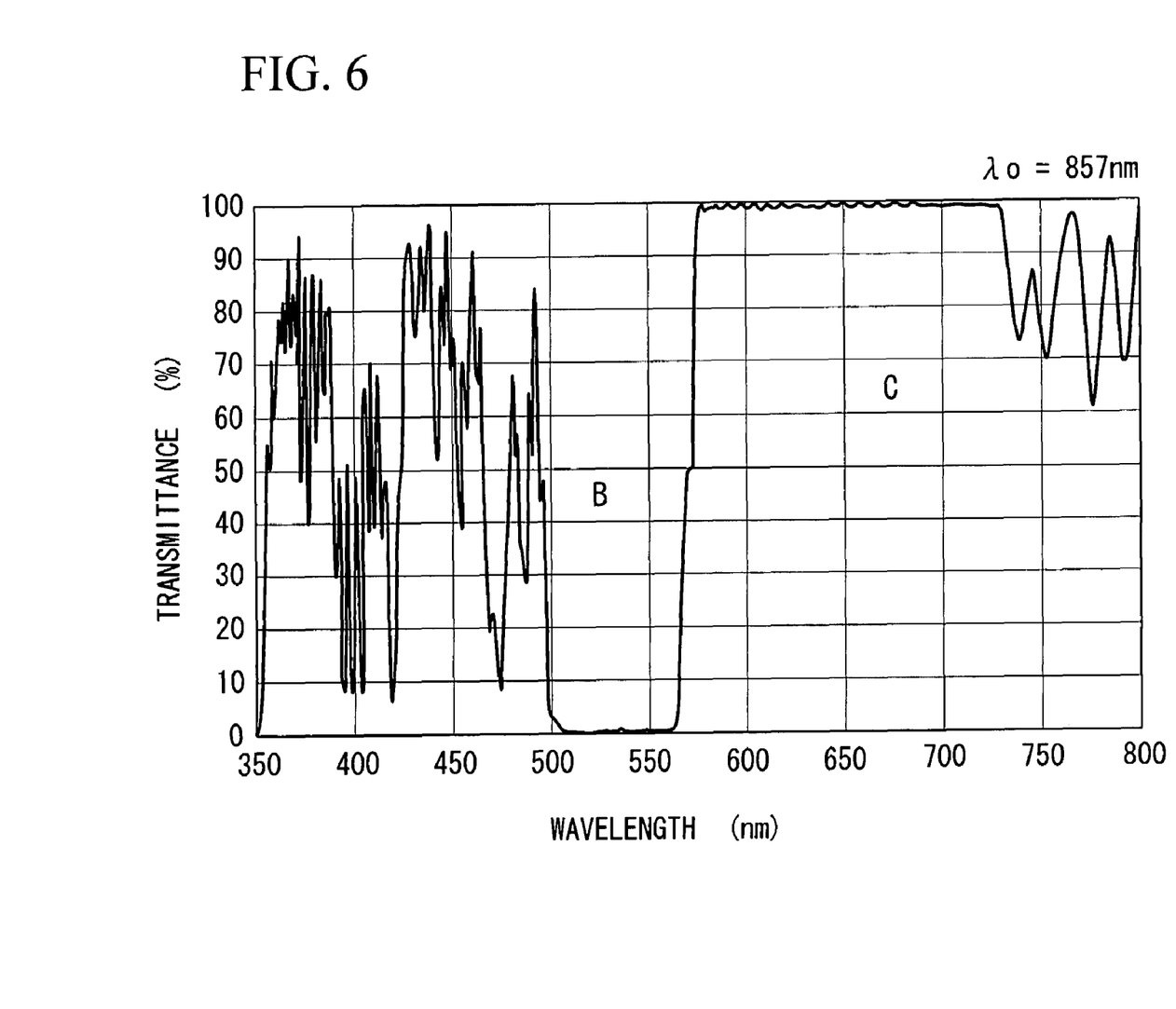
FIG. 6 shows a transmission characteristic of the dichroic mirror in FIG. 3, according to a second Example.

FIG. 6, which assumes a design wavelength $\lambda_0$=857 nm, shows a case where the third-harmonic band is used as the reflection band for excitation light.

The coefficients representing the optical film thickness of each layer are the same as the coefficients in Table 1. However, since value of the design wavelength $\lambda_0$ is different, the optical film thicknesses are different from those in the first Example.

Third Example

Figure 7:
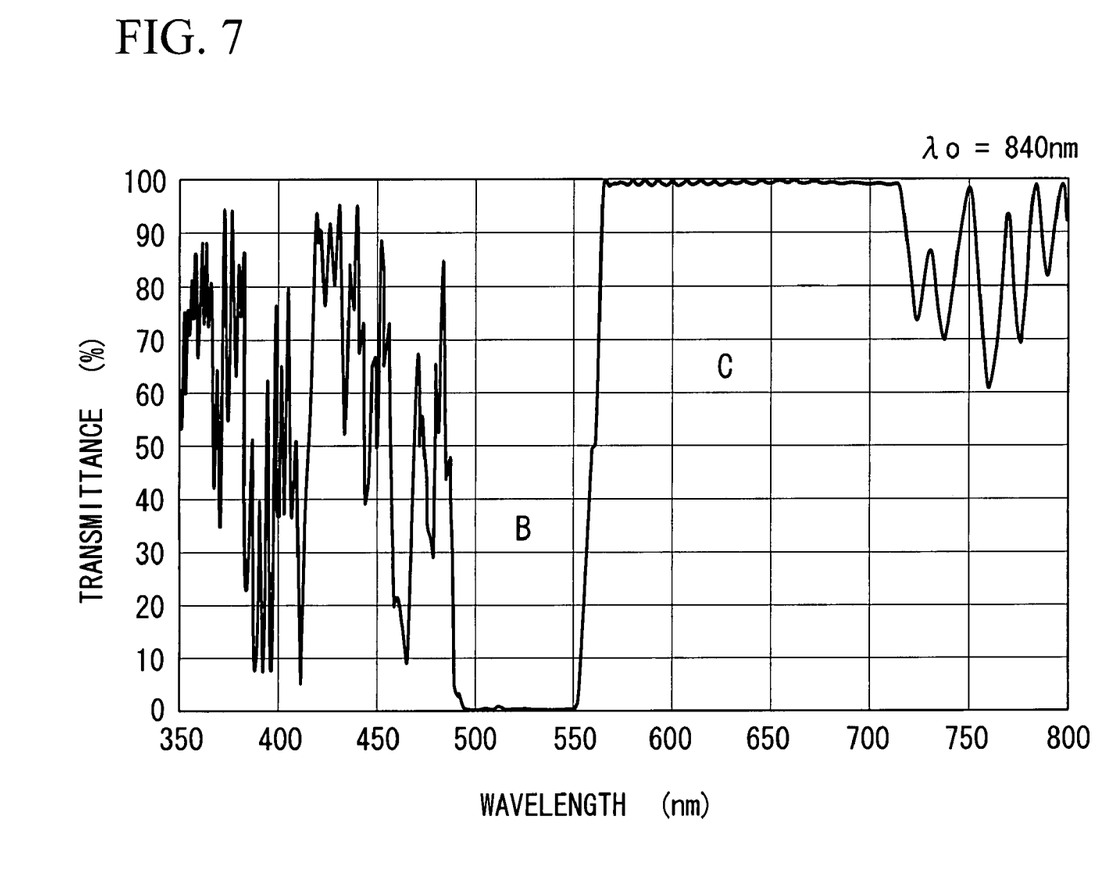
FIG. 7 shows a transmission characteristic of the dichroic mirror in FIG. 3, according to a third Example.

FIG. 7, which assumes a design wavelength $\lambda_0=840$ nm, shows a case where the third-harmonic band is used as the reflection band for excitation light.

The coefficients representing the optical film thicknesses of each layer are the same as the coefficients in Table 1. However, since the value of the design wavelength $\lambda_0$ is different, the optical film thicknesses are different from those in the first and second Examples.

Fourth Example

Figure 8:
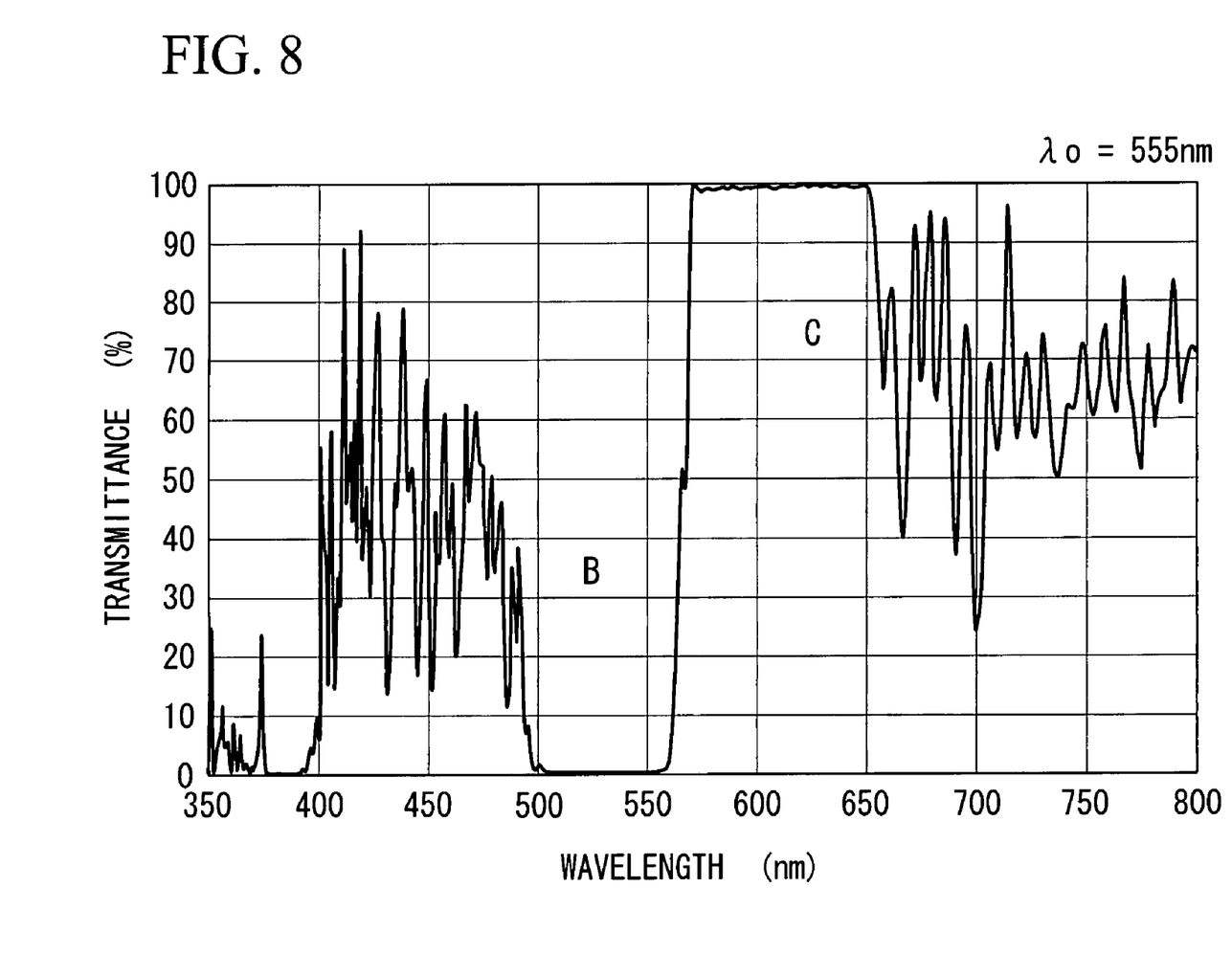
FIG. 8 shows a transmission characteristic of the dichroic mirror in FIG. 3, according to a fourth Example.

Table 2 and FIG. 8, which assume a design wavelength $\lambda_0=555$ nm, show a case in which the third-harmonic band is used as the reflection band for excitation light.

TABLE 2

| LAYER NUMBER | TYPE | $\lambda_0 = 555$ nm OPTICAL FILM THICKNESS ($\times\lambda_0/4$) |
|---|---|---|
| 1 | H | 1.88597 |
| 2 | L | 2.18669 |
| 3 | H | 1.41554 |
| 4 | L | 1.36297 |
| 5 | H | 0.14271 |
| 6 | L | 0.85466 |
| 7 | H | 1.71892 |
| 8 | L | 1.57693 |
| 9 | H | 0.261 |
| 10 | L | 0.51077 |
| 11 | H | 0.88631 |
| 12 | L | 0.19587 |
| 13 | H | 0.47337 |
| 14 | L | 1.15063 |
| 15 | H | 1.18957 |
| 16 | L | 0.34309 |
| 17 | H | 2.40938 |
| 18 | L | 2.0157 |
| 19 | H | 2.16363 |
| 20 | L | 2.10978 |
| 21 | H | 2.38709 |
| 22 | L | 2.06774 |
| 23 | H | 2.33683 |
| 24 | L | 2.09999 |
| 25 | H | 2.26976 |
| 26 | L | 2.05093 |
| 27 | H | 2.34533 |
| 28 | L | 2.02421 |
| 29 | H | 2.3548 |
| 30 | L | 2.02632 |
| 31 | H | 2.36659 |
| 32 | L | 1.97933 |
| 33 | H | 2.3338 |
| 34 | L | 1.97598 |
| 35 | H | 2.40989 |
| 36 | L | 1.94765 |
| 37 | H | 2.36059 |
| 38 | L | 1.94378 |
| 39 | H | 2.39307 |
| 40 | L | 1.99428 |
| 41 | H | 2.40554 |
| 42 | L | 1.93888 |
| 43 | H | 2.37095 |
| 44 | L | 1.93708 |
| 45 | H | 2.40083 |
| 46 | L | 2.00365 |
| 47 | H | 2.4098 |
| 48 | L | 1.8752 |
| 49 | H | 2.41724 |
| 50 | L | 1.85543 |
| 51 | H | 2.39793 |
| 52 | L | 2.02099 |
| 53 | H | 2.43976 |
| 54 | L | 1.86106 |
| 55 | H | 2.40138 |
| 56 | L | 1.91827 |
| 57 | H | 2.45763 |
| 58 | L | 1.82816 |
| 59 | H | 2.41354 |
| 60 | L | 1.91057 |
| 61 | H | 2.49702 |
| 62 | L | 1.79504 |
| 63 | H | 2.38892 |
| 64 | L | 1.91133 |
| 65 | H | 2.50415 |
| 66 | L | 1.7709 |
| 67 | H | 2.44177 |
| 68 | L | 1.93878 |
| 69 | H | 2.40514 |
| 70 | L | 1.79033 |
| 71 | H | 2.48284 |
| 72 | L | 2.02427 |
| 73 | H | 2.70903 |
| 74 | L | 0.99132 |
| 75 | H | 2.77159 |
| 76 | L | 1.60158 |
| 77 | H | 2.71964 |
| 78 | L | 1.34518 |
| 79 | H | 2.62327 |
| 80 | L | 1.38374 |
| 81 | H | 2.81895 |
| 82 | L | 1.14883 |
| 83 | H | 2.831 |
| 84 | L | 0.80233 |
| 85 | H | 3.27208 |
| 86 | L | 0.79146 |
| 87 | H | 2.7581 |
| 88 | L | 1.41967 |
| 89 | H | 2.72482 |
| 90 | L | 1.40722 |
| 91 | H | 2.65425 |
| 92 | L | 1.27932 |
| 93 | H | 2.82677 |
| 94 | L | 1.2785 |
| 95 | H | 2.73852 |
| 96 | L | 1.30652 |
| 97 | H | 2.69464 |
| 98 | L | 1.28185 |
| 99 | H | 2.74279 |
| 100 | L | 1.12317 |
| 101 | H | 2.58138 |
| 102 | L | 1.36394 |
| 103 | H | 2.46775 |
| 104 | L | 1.20603 |
| 105 | H | 0.20775 |
| 106 | L | 0.49535 |
| 107 | H | 1.08679 |
| 108 | L | 0.27578 |
| 109 | H | 0.52047 |
| 110 | L | 0.48929 |
| 111 | H | 0.48579 |
| 112 | L | 0.51099 |
| 113 | H | 0.52576 |
| 114 | L | 0.2142 |
| 115 | H | 0.44626 |
| 116 | L | 0.68167 |
| 117 | H | 0.23826 |
| 118 | L | 0.53545 |
| 119 | H | 0.51385 |
| 120 | L | 0.43578 |
| 121 | H | 0.31794 |
| 122 | L | 0.64872 |
| 123 | H | 2.31699 |
| 124 | L | 2.05053 |
| 125 | H | 2.59352 |
| 126 | L | 1.76077 |
| 127 | H | 1.91204 |
| 128 | L | 0.70659 |

Fifth Example

Figure 9:
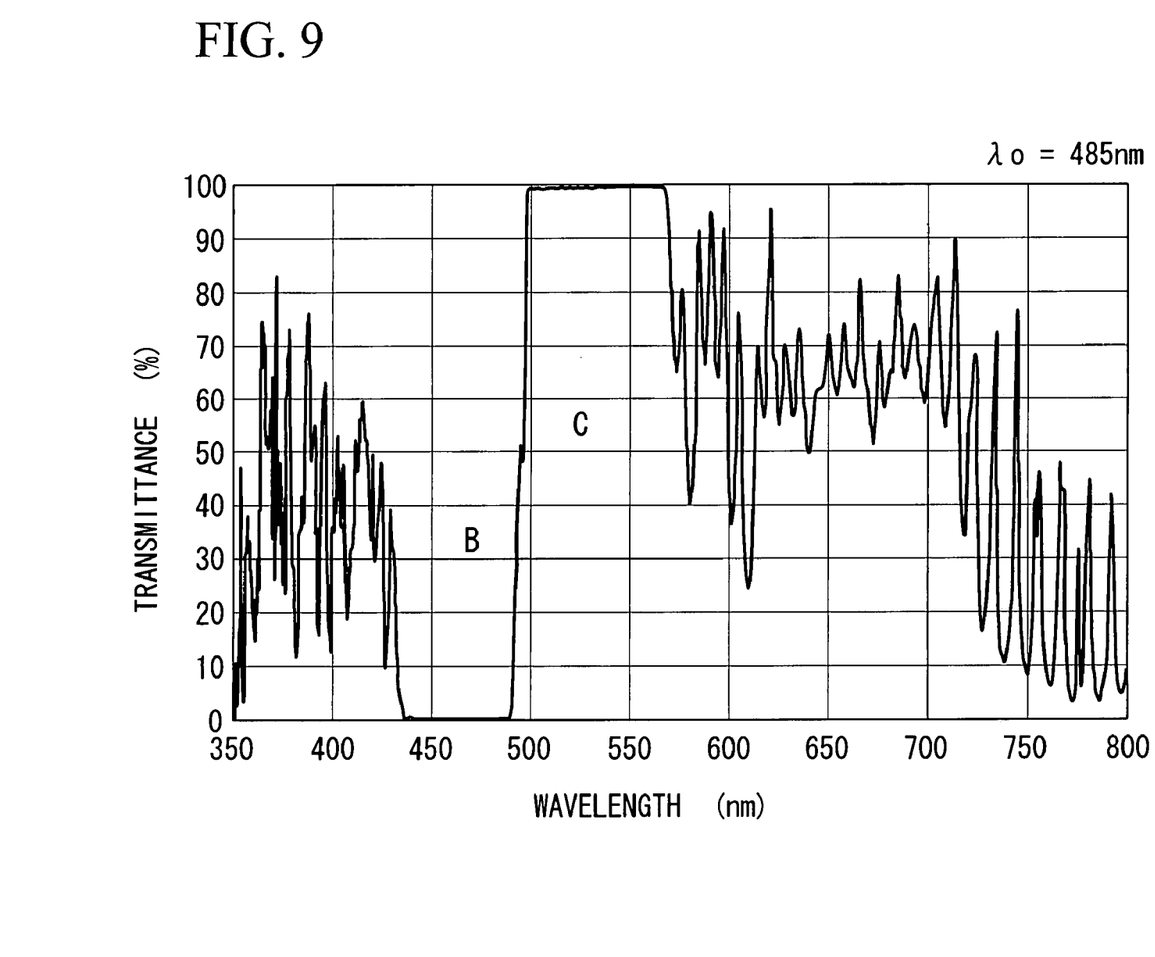
FIG. 9 shows a transmission characteristic of the dichroic mirror in FIG. 3, according to a fifth Example.

FIG. 9 shows a case in which the design wavelength $\lambda_0=485$ nm.

The coefficients representing the optical film thicknesses of each layer are the same as the coefficients shown in Table 2. However, since the value of the design wavelength $\lambda_0$ is different, the optical film thicknesses are different from those in the fourth Example.

According to these Examples, it is possible to form a dichroic mirror 10 having an ideal transmission characteristic F3 which sharply rises from the reflection band B where the transmittance is approximately 0% to the fluorescence-transmitting band C where the transmittance is approximately 100%, which exhibits an extremely small step due to splitting of P-polarized and S-polarized light, and in which the fluorescence-transmitting band C extends to comparatively long wavelengths.

Sixth Example

In the fluorescence filter set 4 described above, it is possible to use a laser light source instead of the first optical filter 9. In such a case, possible wavelengths of the laser light source include, for example, 488 nm, 512 nm, 543 nm, and 633 nm. The light from such a laser light source, serving as the excitation light L2, is reflected by the dichroic mirror 10 and produces fluorescence L3 when irradiating the specimen A. By using a laser light source, excitation light L2 having high wavelength purity can be obtained, which allows highly efficient fluoroscopy to be carried out.

What is claimed is:

1. A dichroic mirror comprising:
    a transparent substrate; and
    a dielectric multilayer film formed by alternately laminating high-refractive-index layers and low-refractive-index layers on the transparent substrate;
    wherein the dielectric multilayer film includes from 50 to 150 alternately laminated high-refractive-index layers and low-refractive-index layers each having an optical film thickness from $1.5\lambda_0/4$ to $2.5\lambda_0/4$, where $\lambda_0$ is a design wavelengths;
    the dichroic mirror having a reflection band located at wavelengths shorter than the design wavelength, and the dichroic mirror having a transmitting band located at wavelengths longer than the design wavelength, wherein a wavelength gap exists between the reflection band and the transmitting band;
    the average reflectance in the reflection band is 0.1% or less;
    the transmittance in the transmitting band existing in a different wavelength band from the reflection band is 80% or greater; and
    the wavelength gap between the reflection band and the transmitting band is a region of the transmission characteristic of the dichroic mirror where the transmittance exceeds 0.1% and does not exceed 80%, and wherein the wavelength gap is 13 nm or less.

2. A dichroic mirror according to claim 1, wherein:
    when a rear-surface reflection of the transparent substrate is disregarded, the range of an undulation in the transmittance in the transmitting band is 3% or less.

3. A dichroic mirror according to claim 1, further comprising:
    an adjustment layer, formed as a final layer at an air side of the alternating layers, for suppressing the range of an undulation in the transmittance in the transmitting band,
    wherein the film thickness of the adjustment layer is substantially half of the thickness of the other alternating layers.

4. A dichroic mirror according to claim 1, further comprising:
    adjustment layers, formed at the substrate side in addition to the alternating layers, the number of adjustment layers being approximately 20,
    wherein each adjustment layer is formed with a film thickness from $0.1\lambda_0/4$ to $2.2\lambda_0/4$.

5. A dichroic mirror according to claim 1, further comprising:
    adjustment layers, formed at an air side in addition to the alternating layers, the number of adjustment layers being approximately 50.

6. A fluorescence filter set comprising:
    a first wavelength-selecting member for selectively transmitting excitation light of a first wavelength;
    a dichroic mirror according to claim 1, for reflecting the excitation light transmitted by the first wavelength-selecting member in a direction orthogonal to an incident direction and for transmitting fluorescence returning from the reflection direction; and
    a second wavelength-selecting member for selectively transmitting the fluorescence transmitted by the dichroic mirror.

7. A fluorescence filter set comprising:
    a dichroic mirror according to claim 1, for reflecting incident light in a direction orthogonal to the incident direction and for transmitting fluorescence returning from the reflection direction; and
    a wavelength-selecting member for selectively transmitting the fluorescence transmitted by the dichroic mirror.

8. A fluoroscopy apparatus comprising:
    a light source;
    a fluorescence filter set according to claim 6, for reflecting excitation light from the light source and for transmitting fluorescence returning from the reflection direction;
    an objective optical system for irradiating a specimen with the excitation light reflected by the fluorescence filter set; and
    an observation optical system for observing the fluorescence returning from the specimen and transmitted by the objective optical system and the fluorescence filter set.

9. A fluoroscopy apparatus comprising:
    a light source;
    a fluorescence filter set according to claim 6, for reflecting excitation light from the light source and for transmitting fluorescence returning from the reflection direction;
    an objective optical system for irradiating a specimen with the excitation light reflected by the fluorescence filter set; and
    an observation optical system for observing the fluorescence returning from the specimen and transmitted by the objective optical system and the fluorescence filter set.

10. A dichroic mirror for use in fluorescence microscope, comprising:

a transparent substrate made of glass materials that do no use lead; and a dielectric multilayer film formed by alternately laminating high-refractive-index layers and low-refractive-index layers on the transparent substrate;

wherein the high-refractive-index layers are formed of a high-refractive-index material with a refractive index of 2.0 or more;

the low-refractive-index layers are formed of a low-refractive-index material with a refractive index of 1.5 or less; and the dielectric multilayer film includes more than 50 alternately laminated high-refractive-index layers and low-refractive-index layers;

the dichroic mirror having a reflection band located at a wavelength band of a second harmonic or higher, which appears at the short wavelength side of the design wavelength, and the dichroic mirror having a transparent band located at wavelength near the reflection band; and wherein the transparent band is located at a wavelength longer than a longest wavelength of the reflection band; and the design wavelength is a first-harmonic central wavelength at an incident angle of 0°;

the average reflectance in the reflection band is 0.1% or less;

the transmittance in the transmitting band existing in a different wavelength band from the reflection band is 80% or greater; and the wavelength gap between the reflection band and the transmitting band is a region of the transmission characteristic of the dichroic mirror where the transmittance exceeds 0.1% and does not exceed 80%, and wherein the wavelength gap is 13 nm or less.

* * * * *